United States Patent
Larnard et al.

(10) Patent No.: US 6,923,826 B2
(45) Date of Patent: *Aug. 2, 2005

(54) NEUROSURGICAL DEVICE FOR THERMAL THERAPY

(75) Inventors: Donald J. Larnard, Hampton Falls, NH (US); Dan Sachs, Boston, MA (US)

(73) Assignee: Seacoast Technologies, Inc., Portsmouth, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/660,157

(22) Filed: Sep. 11, 2003

(65) Prior Publication Data

US 2004/0049250 A1 Mar. 11, 2004

Related U.S. Application Data (63) Continuation of application No. 09/971,072, filed on Oct. 4, 2001, now Pat. No. 6,648,907.
(60) Provisional application No. 60/238,314, filed on Oct. 5, 2000.

(51) Int. Cl.$^7$ ................................................. A61F 7/12
(52) U.S. Cl. .......................... 607/105; 607/96; 607/113
(58) Field of Search ................................. 607/105–113

(56) References Cited

U.S. PATENT DOCUMENTS

| | | |
|---|---|---|
| 2,190,384 A | 2/1940 | Newman |
| 3,170,465 A | 2/1965 | Henney et al. |
| 3,174,841 A | 3/1965 | Seaman |
| 3,220,414 A | 11/1965 | Johnston |
| 3,504,674 A | 4/1970 | Swenson et al. |
| 3,736,936 A | 6/1973 | Basiulis et al. |
| 3,776,241 A | 12/1973 | Magliton et al. |
| 3,848,607 A | 11/1974 | St. Clair |
| 3,897,790 A | 8/1975 | Magliton et al. |
| 4,010,795 A | 3/1977 | Steinberg |
| 4,207,897 A | 6/1980 | Lloyd et al. |
| 4,719,919 A | 1/1988 | Marchosky et al. |
| 4,781,193 A | 11/1988 | Pagden |
| 4,860,744 A | 8/1989 | Johnson et al. |
| 4,946,460 A | 8/1990 | Merry et al. |
| 4,989,601 A | 2/1991 | Marchosky et al. |
| 5,108,407 A | 4/1992 | Geremia et al. |
| 5,207,674 A | 5/1993 | Hamilton |
| 5,209,227 A | 5/1993 | Deutsch |
| 5,261,399 A | 11/1993 | Klatz et al. |
| 5,304,214 A | 4/1994 | DeFord et al. |
| 5,334,181 A | 8/1994 | Rubinsky et al. |
| 5,380,319 A | 1/1995 | Saito et al. |

(Continued)

FOREIGN PATENT DOCUMENTS

| | | |
|---|---|---|
| JP | 11-170076 | 11/2000 |
| JP | 2000/126973 | 12/2000 |
| JP | 11-290530 | 4/2001 |

(Continued)

OTHER PUBLICATIONS

Perov, et al., "Design of Thermodes for Cooling Sites of Cerebral Hemisphere Cortex in Chronic Tests", Sechenov Physiology Journal of the USSR, No. 7, 1983, Methods of Physiological Investigations, 5 pgs.

(Continued)

*Primary Examiner*—Roy D Gibson
*Assistant Examiner*—Henry M Johnson, III
(74) *Attorney, Agent, or Firm*—Christopher & Weisberg, P.A.

(57) ABSTRACT

A device for thermally affecting tissue of a patient includes a housing defining an interior volume that is at least partially insertable into an exterior opening in a patient. A thermal member positioned within the interior volume of the housing includes a thermal input side and a thermal output side to impart a thermal change to the tissue.

14 Claims, 4 Drawing Sheets

U.S. PATENT DOCUMENTS

| | | |
|---|---|---|
| 5,417,686 A | 5/1995 | Peterson et al. |
| 5,429,582 A | 7/1995 | Williams |
| 5,474,533 A | 12/1995 | Ward et al. |
| 5,520,682 A | 5/1996 | Baust et al. |
| 5,531,776 A | 7/1996 | Ward et al. |
| 5,540,711 A | 7/1996 | Kieturakis et al. |
| 5,549,559 A | 8/1996 | Eshel |
| 5,591,162 A | 1/1997 | Fletcher et al. |
| 5,607,443 A | 3/1997 | Kieturakis et al. |
| 5,609,620 A | 3/1997 | Daily |
| 5,611,767 A | 3/1997 | Williams |
| 5,624,392 A | 4/1997 | Saab |
| 5,643,207 A | 7/1997 | Rise |
| 5,645,528 A | 7/1997 | Thome |
| 5,713,923 A | 2/1998 | Ward et al. |
| 5,716,353 A | 2/1998 | Matsuura et al. |
| 5,716,386 A | 2/1998 | Ward et al. |
| 5,718,584 A | 2/1998 | Wong |
| 5,718,684 A | 2/1998 | Gupta |
| 5,730,756 A | 3/1998 | Kieturakis et al. |
| 5,735,817 A | 4/1998 | Shantha |
| 5,772,680 A | 6/1998 | Kieturakis et al. |
| 5,814,123 A | 9/1998 | Hansen |
| 5,817,123 A | 10/1998 | Kieturakis et al. |
| 5,843,075 A | 12/1998 | Taylor |
| 5,871,498 A | 2/1999 | Jervis et al. |
| 5,891,134 A | 4/1999 | Goble et al. |
| 5,899,898 A | 5/1999 | Arless et al. |
| 5,913,885 A | 6/1999 | Klatz et al. |
| 5,916,212 A | 6/1999 | Baust et al. |
| 5,916,242 A | 6/1999 | Schwartz |
| 5,928,203 A | 7/1999 | Davey et al. |
| 5,951,512 A | 9/1999 | Dalton |
| 5,954,714 A | 9/1999 | Saadat et al. |
| 5,957,963 A | 9/1999 | Dobak, III |
| 5,972,924 A | 10/1999 | Keep et al. |
| 5,976,109 A | 11/1999 | Heruth |
| 6,004,337 A | 12/1999 | Kieturakis et al. |
| 6,015,382 A | 1/2000 | Zwart et al. |
| 6,015,421 A | 1/2000 | Echeverry et al. |
| 6,017,324 A | 1/2000 | Tu et al. |
| 6,030,412 A | 2/2000 | Klatz et al. |
| 6,042,579 A | 3/2000 | Elsberry et al. |
| 6,045,532 A | 4/2000 | Eggers et al. |
| 6,051,019 A | 4/2000 | Dobak, III |
| 6,053,913 A | 4/2000 | Tu et al. |
| 6,073,051 A | 6/2000 | Sharkey et al. |
| 6,074,412 A | 6/2000 | Mikus et al. |
| 6,083,148 A | 7/2000 | Williams |
| 6,090,132 A | 7/2000 | Fox |
| 6,096,068 A | 8/2000 | Dobak, III et al. |
| 6,106,518 A | 8/2000 | Wittenberger et al. |
| 6,113,593 A | 9/2000 | Tu et al. |
| 6,117,128 A | 9/2000 | Gregory |
| 6,122,549 A | 9/2000 | Sharkey et al. |
| 6,123,718 A | 9/2000 | Tu et al. |
| 6,126,680 A | 10/2000 | Wass |
| 6,126,684 A | 10/2000 | Gobin et al. |
| 6,129,736 A | 10/2000 | Jervis et al. |
| 6,132,415 A | 10/2000 | Finch et al. |
| 6,146,411 A | 11/2000 | Noda et al. |
| 6,149,677 A | 11/2000 | Dobak, III |
| 6,152,920 A | 11/2000 | Thompson et al. |
| 6,156,057 A | 12/2000 | Fox |
| 6,168,608 B1 | 1/2001 | Echeverry et al. |
| 6,179,831 B1 | 1/2001 | Bliweis |
| 6,183,501 B1 | 2/2001 | Latham |
| 6,224,624 B1 | 5/2001 | Lasheras et al. |
| 6,238,428 B1 | 5/2001 | Werneth et al. |
| 6,248,126 B1 | 6/2001 | Lesser et al. |
| 6,251,129 B1 | 6/2001 | Dobak, III et al. |
| 6,251,130 B1 | 6/2001 | Dobak, III et al. |
| 6,277,143 B1 * | 8/2001 | Klatz et al. ............... 607/104 |
| 6,322,559 B1 | 11/2001 | Daulton et al. |
| 6,383,210 B1 | 5/2002 | Magers et al. |

FOREIGN PATENT DOCUMENTS

| | | |
|---|---|---|
| RU | SU211736 | 11/1968 |
| RU | SU293381 | 1/1969 |
| RU | SU432907 | 7/1972 |
| RU | SU639557 | 5/1975 |
| RU | SU833266 | 11/1978 |
| RU | SU1138152 A | 9/1983 |
| RU | SU1544422 A1 | 5/1988 |
| RU | SU1745238 A1 | 7/1990 |
| RU | SU1787026 A3 | 8/1990 |
| RU | 2100989 C1 | 1/1998 |
| WO | WO 96/03943 | 2/1996 |
| WO | WO 99/34758 | 7/1999 |
| WO | WO 00/07507 | 2/2000 |
| WO | WO 00/59419 | 10/2000 |
| WO | WO 01/17471 | 3/2001 |
| WO | WO 01/76517 | 10/2001 |

OTHER PUBLICATIONS

Locke, et al., "*Profound Selective Arterial Cooling of Brain without Pump or Oxygenator*", Surgical Forum, 1965, 16: pp. 421–422.

Negrin, "*An Instrument to Obtain Lcoal Hypothermia of the Brain or Spinal Cord*", International Surgery, Aug. 1970, vol. 54, No. 2, pp. 93–106.

Mursky, "*On the Use of Complex (Cranial Cerebral and General) Hypothermia in Experiments*", Brain Hypothermia, 1965, 4 pgs.

Shilo, et al., "*Delivery/Dialysis Cannula for Local Superfusion of Brain Structures at Cranial Cerebral Hypothermia*", Collection of Scientific Works, 1988, 3 pgs.

Rybakov, "*Method of Intra–Ventricle Hypothermia of Brain*", 3 pgs.

* cited by examiner

NEUROSURGICAL DEVICE FOR THERMAL THERAPY

CROSS-REFERENCE TO RELATED APPLICATION

This application is related to and is a continuation of allowed U.S. patent application Ser. No. 09/971,072, filed Oct. 4, 2001, U.S. Pat. No. 6,648,907, entitled NEUROSURGICAL DEVICE FOR THERMAL THERAPY, which is related to and claims priority to U.S. Provisional Patent Application Ser. No. 60/238,314, Filed Oct. 5, 2000, entitled SYSTEMS AND METHODS FOR CONTROLLING TEMPERATURE OF BRAIN TISSUE, the entirety of all of which are incorporated herein by reference.

STATEMENT REGARDING FEDERALLY SPONSORED RESEARCH OR DEVELOPMENT n/a

FIELD OF THE INVENTION

The present invention relates to systems and methods for controlling brain tissue temperature, and in particular to systems and methods for subcranial temperature control of brain tissue through the use of contact cooling devices.

BACKGROUND OF THE INVENTION

Many of the advantages of reducing or raising the temperature of a body tissue are well known. It has been found particularly desirable to lower the temperature of the body in order to reduce the metabolism of the body. In stroke and several other pathological conditions, lowering the temperature of a body also reduces the permeability of the blood/brain barrier. Reduced body temperature also inhibits release of damaging neurotransmitters and inhibits calcium-mediated effects. Further, reduced body temperature has been found to inhibit brain edema and lower intracranial pressure. These and other advantageous effects of reduced body temperature are known in the art.

Prior art devices and methods affect a thermal change in a body by a systemic approach, meaning that the overall temperature of the entire body is lowered or raised to achieve the advantages noted above. Cooling the body has been particularly effective in surgical applications where reducing metabolism has made it possible to more easily accommodate lengthy operative procedures. An example of this systemic approach includes catheters for transferring heat to or from blood flowing within a patient's vessel. Closed loop heat exchange catheters are also known. Some of the disadvantages of systemic temperature reduction include the stimulation of cardiac arrhythmia, pulmonary edema and coagulopathies. Systemic temperature reduction also results in hypotension and immune suppression.

Further, a systemic approach is not always advantageous when the beneficial effects are desired locally at the focus of the operative procedure and only the disadvantages of temperature reduction are felt throughout the remainder of the body. As such, recent focus has been directed to producing reduced temperature in localized areas of the body, leaving the remainder of the body to function at a normal body temperature. Localized temperature reduction in known devices relies on the control of temperature through a wholly external device, for example using cooling helmets or cooling neck collars to produce localized temperature reduction for the brain. However, there are disadvantages associated with external cooling to affect internal tissue. For example, external methods do not allow a high enough resolution to allow selective tissue cooling. Some of the same disadvantages that are associated with thermally affecting the whole body can occur when using external cooling. When it is advantageous to apply thermal energy to a specified tissue location and not to other regions, the known external devices and their accompanying methods can not adequately accommodate these needs.

Therefore it is desirable to have a device and method for localized temperature control of a body part. Further, it is desirable to provide a way to apply thermal energy to a specific area of tissue, such as the brain, which is not ordinarily directly external to the body in a manner which minimizes trauma and the size of the body opening which must be created to access the tissue area.

SUMMARY OF THE INVENTION

The present invention overcomes the disadvantages of known systemic and external devices and techniques by providing localized brain cooling with a device placed through the skull.

The present invention provides a device and method for localized temperature control of a body part, such as the brain. In an exemplary embodiment, a device for thermally affecting tissue of a patient includes a housing defining an interior volume that is at least partially insertable into an exterior opening in a patient, such as a burr hole though the skull. A thermal member positioned within the interior volume of the housing includes a thermal input side and a thermal output side to impart a thermal change to the tissue. An exemplary method of treatment using the device includes the steps of exposing tissue to be thermally affected; attaching a thermal device to an anchor point of the body; positioning the thermal member near or on the tissue; and operating the thermal member to thermally change the temperature of the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a device for transferring thermal energy to or from a localized region of a body tissue. Referring now to the drawing figures in which like reference designators refer to like elements, there is shown FIG. 1 a perspective view of an exemplary embodiment of a device constructed in accordance with the principles of the present invention and designated generally as device 10. The device 10 has a housing 12 with a first end 14, a second end 16 and an optional circulation vent 18 for the intake and outlet of a thermally conductive fluid or ambient air. The housing 12 can be constructed of any suitable material, for example metals, plastics or a combination thereof. It is contemplated that the housing 12 has a diameter "D", measured at the widest portion of the device, from less than one centimeter to approximately ten centimeters. In exemplary embodiments, the diameter ranges from approximately one centimeter to approximately two centimeters. Optional radial threads 20 are provided on the exterior of the housing 12 to facilitate attachment to bone structure such as a skull. However, it is contemplated that non-threaded arrangements can also be provided or coupled to or on the housing 12, for example, flutes, barbs, ridges or other such elements. Expandable elements can also be used to seal the device to bone structures, such as the skull.

Figure 2:
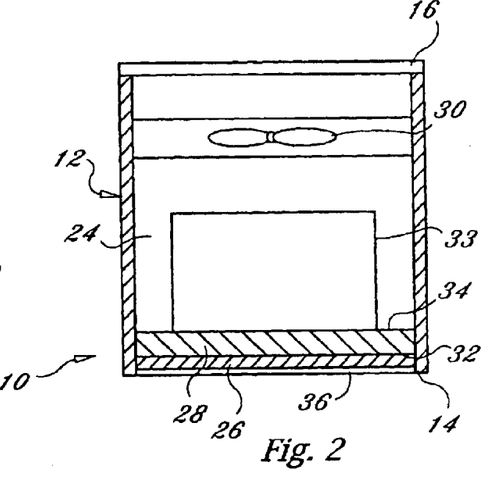
FIG. 2 is a section view taken along section 2—2 of FIG. 1.

FIG. 2 is a section view taken along section 2—2 of FIG. 1. The housing 12 is arranged as a circumferential wall which defines an interior space 24. Provided within the interior space 24, starting at the first end 14 and moving toward the second end 16, is a contact member 26 which can be configured to directly contact a tissue or to contact an intermediate material. The contact member 26 can be constructed of any thermally conductive material, for example, stainless steel, aluminum, copper, titanium, combined metals, alloys, various polymers or other such materials. Additionally, adjacent the contact member 26 is a thermal member 28. The thermal member 28 has a thermal input side 32 in thermal communication with the contact member 26 and a thermal output side 34. The thermal member 28 can be a thermo-electric cooler, for example, a peltier-effect cooler. Optionally, a thermal dissipation member 33 is provided in thermal communication with the thermal output side 34 of the thermal member 28. Such devices are known in the art, for example a common thermal dissipation member is a heat sink. However, many alternate components for dissipating thermal energy can be provided.

Alternatively, the thermal member 28 can be configured to directly contact a tissue or to contact an intermediate material. The input side 32 of the thermal member 28 can be in thermal communication with a tissue or an intermediate material.

Further provided within the housing 12 in the interior space 24 is a fluid circulation member 30. The term "fluid" as used herein generally refers to any flowable substance, including but not limited to gases and liquids. An exemplary fluid circulation member 30 is a cooling fan. The fluid circulation member 30 is positioned such that it circulates a fluid, such as air, across the thermal output side 34 of the thermal member 28 or the optional thermal dissipation member 33 if provided, thereby removing thermal energy dissipated by the thermal member 28. Alternatively, it is contemplated that a pump used in association with a thermally conductive liquid can be provided to dissipate thermal energy generated by the output side 34 of the thermal member 28.

In addition, an optional membrane 36 is provided in thermal communication with the contact member 26 or the thermal member 28. Membrane 36 can be constructed of any bio-compatible material and can be constructed to directly contact tissue.

Referring to FIG. 2, the operation of an exemplary device is now discussed in detail. Power is supplied to the thermal member 28 through electrical wires (not shown) which in turn creates a thermal input side 32 and a thermal output side 34 to the thermal member 28 (the thermal member discussed here is a peltier effect cooler and its function is well known in the art). By operation of the thermal member 28, the thermal input side 32 has a reduced temperature relative to the thermal output side 34 which causes a cooling effect at the thermal input side 32. The thermal input side 32 being in thermally conductive contact with the contact member 26, thereby causes a reduction of the relative temperature of the contact member 26. The output side 34 being in thermally conductive contact with the optional thermal dissipation member 33 thereby raises the relative temperature of the thermal dissipation member 33 (creating heat). Additionally, power or activation energy is supplied to the fluid distribution member 30 to thereby circulate air through the thermal dissipation member 33 and out of housing 12 through the circulation vent 18. Heat dissipated by the thermal dissipation member 33 is removed and discharged from the housing 12 to maintain a reduced temperature at the contact member 26. As such, the concepts of the present invention provide a device 10 for localized cooling of a tissue in a compact package. Alternatively, such a device can subsequently be used for heating tissue locally by reversing the current to the thermoelectric device.

Figure 3:
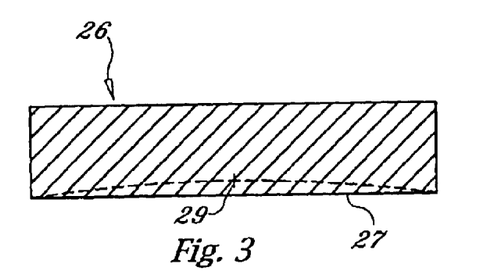
FIG. 3 is a side view of a first end of the device.

FIG. 3 is a side view of an exemplary embodiment of the contact member 26. FIG. 3 shows a contact side 27 having a concave surface as illustrated in phantom line. The amount of curvature can be variable depending on the tissue site to be treated. The concave shape is measured as the center concave distance measured from the contact side 27 perpendicular to a center 29 of the concave region. In exemplary embodiments the concave distance ranges from approximately 0.001 inches to approximately 0.05 inches. In the embodiment shown in FIG. 3, which is placed on the dura mater covering the brain, the concave distance is approximately 0.02 inches.

Figure 4:
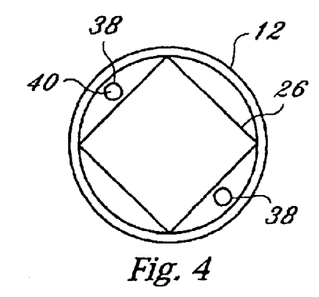
FIG. 4 is an end view of a bottom end of the device.

FIG. 4 illustrates an end view of the first end 14 of the device 10, wherein a square-shaped contact member is disposed within the housing 12. Optionally, one or more access ports 38 are provided for the location of a variety of devices, for example specialty neuro-catheters, thermocouple probes, temperature sensors, pressure sensors or other such devices. Alternatively, an optional insert 40 can be provided to completely or partially obstruct the access port 38. The insert 40 can be constructed from any suitable material, for example, rubber, silicone, aluminum or other such materials. While FIG. 4 shows a square-shaped contact member 26, it is contemplated that various other shapes can be provided. Additionally, an access port (not shown) can also be provided through the contact member 26 itself to accommodate accessory devices as discussed above.

Figure 5:
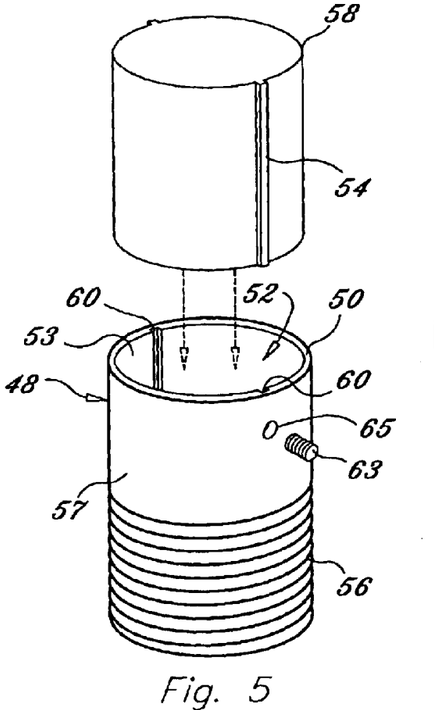
FIG. 5 is a perspective view of another device constructed in accordance with the principles of the invention.

FIG. 5 is an exploded view of another configuration for the device, wherein a housing 48 has a wall 50 that defines an inner volume 52 to receive a thermal cartridge 58. The housing includes longitudinal grooves 54 on the inner surface 53 of the wall 50. Radial threads 56 can be provided for securing the housing 48 to the skull. The thermal cartridge 58 has axial slots 60 configured to be slidably engageable with axial grooves 54 of the housing 48.

The thermal cartridge 58 includes the exemplary elements as discussed above for applying thermal energy to a tissue site, for example, a contact member, a thermal member, and a cooling fan (not shown). In practice, the housing 48 is secured within a skull opening by screwing the radial threads into the bone. The thermal cartridge 58 is then inserted into the inner volume 50 of the housing 48 while aligning the axial slots 60 with the axial grooves 54. The thermal cartridge 58 can be slidably adjusted within the insert housing 48 in order to specifically locate the contact member against the dura matter.

Additionally, the thermal cartridge 58 can be moved in response to dura swelling or shrinkage that may occur during treatment. Once a desired distance of insertion is reached, the thermal cartridge 58 is held in position by a set screw 63 through a screw opening 65 in the insert housing 48. While FIG. 5 illustrates an axial groove and slot arrangement, it is contemplated that alternate configurations can be provided. For example, a spiral groove and slot arrangement can be provided which would provide insertion depth adjustment via rotation of the thermal cartridge relative to the housing.

Figure 6:
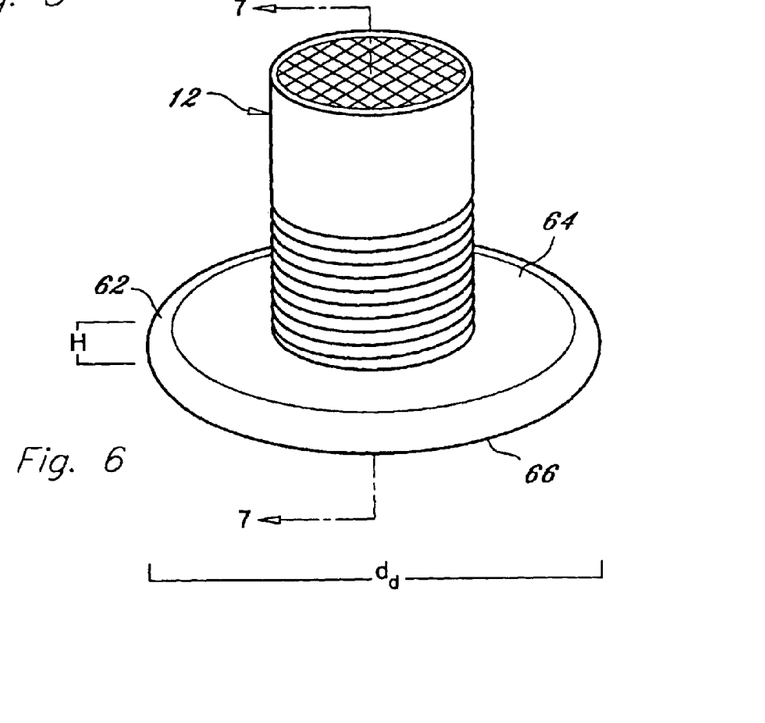
FIG. 6 is another perspective view of a device constructed in accordance with the principles of the invention.

FIG. 6 is a perspective view of another feature of the invention, wherein a surface area expansion element 62 is disposed at the first end 14 of the housing 12. The surface area expansion element 62 provides a tissue contact area that is larger than the contact member 26 (not shown). The surface area expansion element 62 has a height "H" measured from a top 64 to a tissue contact area 66 of the surface area expansion element 62 and a deployed diameter "$d_d$" measured from the widest points at a periphery of the surface area expansion element 62. In an exemplary embodiment, the surface area expansion element 62 has a height to width ratio of approximately one to two. Further, a surface area expansion element 62 constructed in accordance the principles of the present invention can have a deployed diameter $d_d$ ranging in size from 5 to 200 mm. An exemplary embodiment has a deployed diameter of 34 to 48 mm. Another exemplary embodiment has a deployed diameter of 34 to 64 mm. Further, an exemplary embodiment can have a height H ranging in size from 1 to 10 mm. In one exemplary embodiment the height H is approximately 4 mm.

The surface area expansion element 62 can be provided by several different structures, including, for example, an inflatable plenum such as a bladder or balloon. Alternatively, the expansion element 62 can include foldable, rollable, or compressible, ribbons or resilient thermally-conductive structures. Exemplary resilient materials include rubber, silicon, flexible polymers and other materials known in the art. Thus, the surface area expansion element 62 is provided with a structure that allows it to be inserted through a small opening in a body and then deployed to increase the tissue contact area 66. The tissue contact area 66 can have a shape ranging from substantially flat to concave.

Figure 7:
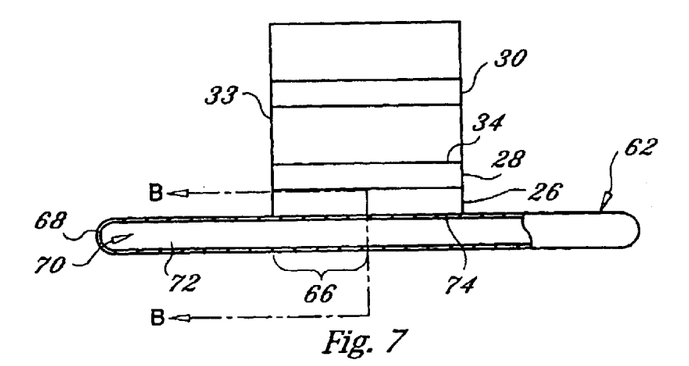
FIG. 7 is a section view taken along section 7—7 of FIG. 6.

FIG. 7 is a sectional view taken along section 7—7 in FIG. 6. FIG. 7 shows the surface area expansion element 62 having a hollow structure. The surface area expansion element 62 has a wall 68 which defines an interior volume 70 which is filled with a thermally transmissive fluid 72. The contact member 26 is in thermal contact with the interior volume 70 via the thermally transmissive fluid 72 at an interface 74. The contact member 26 is in turn in thermal contact with the thermal member 28. Optionally, a thermal dissipation member 33 can be provided in thermal communication with the output side 34 of the thermal member 28. Further the fluid circulation member 30 is provided in fluid communication with the thermal dissipation member 33. In practice, the cooling of the contact member 26 in turn cools the thermally transmissive fluid 72. The thermally transmissive fluid cools the tissue contact area 66 which in turn cools the contacted tissue. In accordance with the principles of the present invention, it is contemplated that the surface area expansion element 62 can have a plethora of shapes, for example a round shape, an oval shape, an oblong shape, a spider-like shape, a spiral shape or an amorphous shape.

Figure 8:
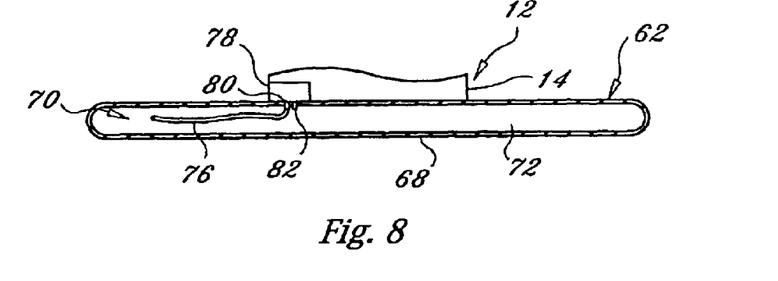
FIG. 8 is a partial sectional view taken along section 8—8 of FIG. 7.

FIG. 8 is a partial sectional view of a device of the invention taken along line B—B in FIG. 7. FIG. 8 shows the surface area expansion element 62 attached to the first end 14 of the housing 12. Further provided within the wall 68, in the interior volume 70 is a hollow injection member 76 having a proximal end and a distal end. A circulation member 78 having an outlet 80 and an inlet 82 is in fluid communication with the proximal end of the injection member 76 via the outlet 80. An example of a circulation member 78 is a fluid pump. An exemplary thermally transmissive fluid 72 is a saline solution or other such fluid. The arrangement of the circulation member 78, the outlet 80, the injection member 76, the inlet 82 and the interior volume 70 define a circulation circuit.

In operation, thermally transmissive fluid 72 is provided within the interior volume 70 and is drawn into the circulation member 78 via the inlet 82. It then is directed through the outlet 80 and in turn the to the proximal end of the injection member 76 to the distal end, which directs the thermally transmissive fluid to a location within the interior volume 70. Alternately, the circulation member 78 can be in thermal contact with the thermal element 28, thereby affecting the temperature of the thermally transmissive fluid directly, or the thermally transmissive fluid can be affected by direct contact with the contact member 26.

Figure 9:
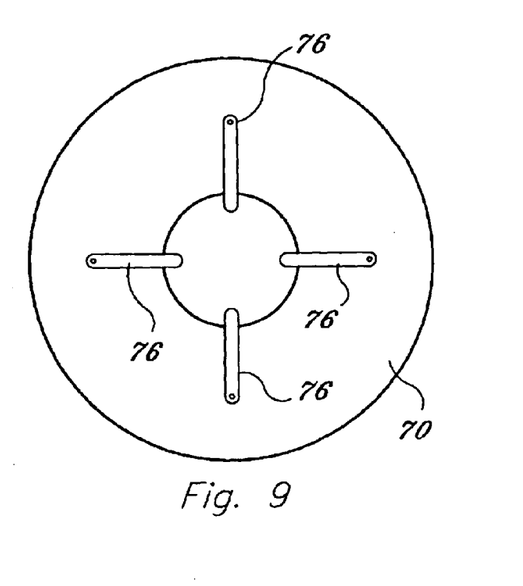
FIG. 9 is an end view of an alternate structure of an expansion element of the device.

FIG. 9 shows an alternate arrangement in which a plurality of injection members 76 are provided within the interior volume 70 to direct thermally transmissive fluid to alternate locations within the interior volume 70. By specifically directing the thermally transmissive fluid a uniform thermal distribution can be provided throughout the interior volume 70.

Figures 10, 11:
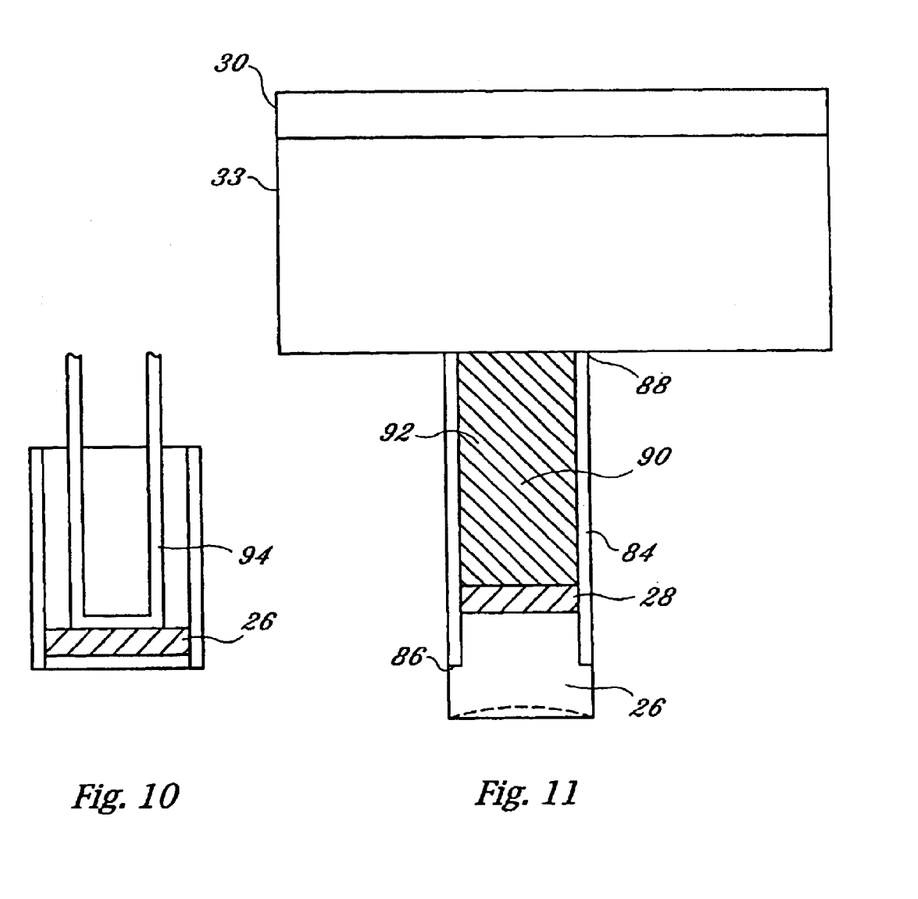
FIG. 10 is a section view of an alternative arrangement of a device constructed in accordance with the principles of the present invention.
FIG. 11 is another section view of still another alternative arrangement of a device constructed in accordance with the principles of the present invention.

FIG. 11 is a sectional view of an alternate arrangement of the thermal cartridge 58 shown in FIG. 5. FIG. 10 shows a cartridge wall 84 having a proximal end 86 and a distal end 88 and defining an interior 90. A contact member 26 is attached to the proximal end 86. Toward the distal end, a thermal member 28 is provided within the interior 90 adjacent and in thermal communication with the contact member 26. Still further toward the distal end 88, a thermal bridge 92 is in thermal communication with the thermal member 28 and is constructed from a thermally transmissive material. Attached to the distal end 88 and in thermal communication with the thermal bridge 92 is a thermal dissipation element 33 which is coupled with a fluid circulation member 30. It is contemplated that the location of the thermal member 28 can alternatively be toward the distal end 88.

The thermal bridge 92 is provided to allow the thermal dissipation member 33 to be spaced a distance from the thermal member 28 or alternatively the contact member 26. In some embodiments it is desirable to have a thermal dissipation member and a fluid circulation member which are larger than the diameter of the housing of the device. By providing a thermal bridge 92, placement of the thermal member 28 or contact member 26 a distance away from the thermal dissipation member 33 is achieved. While the thermal bridge 92 is described in association with the device shown in FIG. 7, it is contemplated that the thermal bridge 92 and expanded thermal dissipation member 33 can be provided in any of the embodiments of the invention.

FIG. 10 illustrates another cartridge configuration for thermal transfer, wherein a fluid conduit 94 is provided in thermal communication with the thermal output side 34 of a thermal dissipation member 33. In practice, a thermally transmissive fluid is circulated through the fluid conduit 94. When the fluid transits the portion of the fluid conduit that is in thermal communication with the thermal output side 34, thermal energy is dissipated to the fluid which is then circulated to a remote fluid chiller and then re-circulated through the fluid conduit 94.

Figure 1:
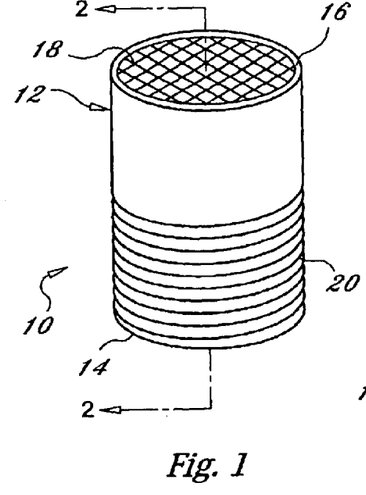
FIG. 1 is a perspective view of an exemplary embodiment of a device constructed in accordance with the principles of the present invention.
Figure 12:
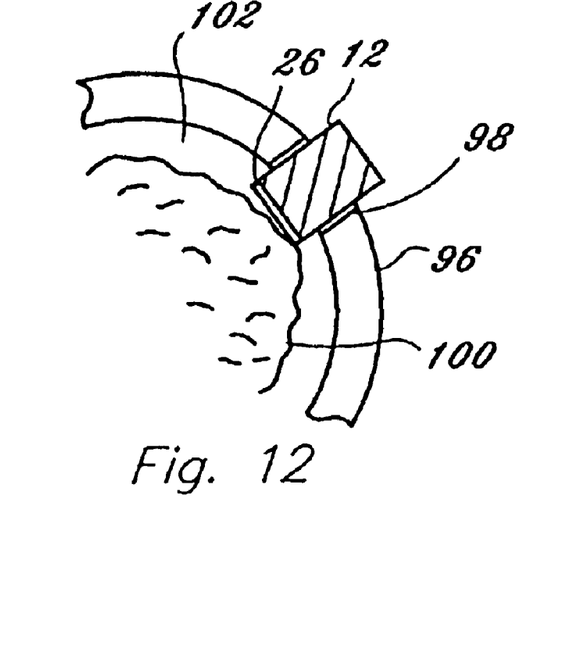
FIG. 12 is a side view of the exemplary device of FIG. 1 shown engaged with a skull.

FIG. 12 depicts a device 10, such as shown in FIG. 1, screwed into a burr hole 98 in a skull 96, wherein a contact element 26 is in thermally conductive contact with dura tissue 100 at a location where treatment is desired.

Figure 13:
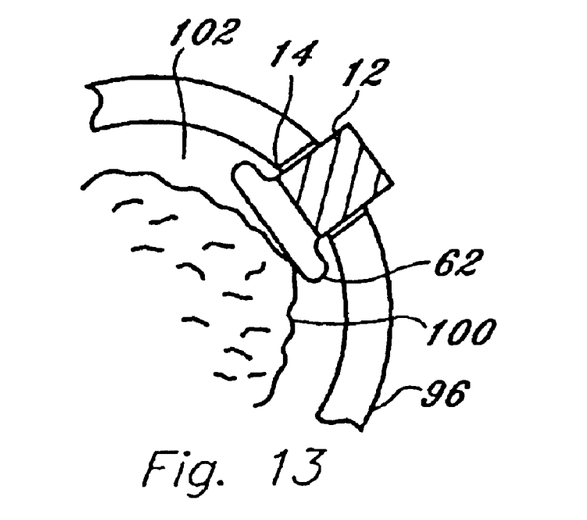
FIG. 13 is a side view of the exemplary device of FIG. 8 shown engaged with a skull.

FIG. 13 depicts a device 10, such as shown in FIG. 8, shown screwed into a burr hole 98 in a skull 96. Attached to the first end 14 of the device 10 is a surface area expansion element 62. The surface area expansion element 62 is configured to fit within a space 102 between the dura tissue 100 and the skull 96 without substantially damaging dura tissue 100. For example, in order to fit within the space 102, the surface area expansion element 62 can have a flattened configuration as described in more detail herein. In an alternate embodiment, such a surface area expansion element 62 can be configured to be placed into subdural space within a body to be treated.

The present invention provides a thermocooler based device which is used to impart a thermal change on a tissue medium. The present invention advantageously provides a user with an ability to control the temperature of a localized region of brain tissue. A procedure using the thermocooling device is accomplished by inserting the device into a burr hole in the skull. An exemplary application is to directly contact the brain tissue with the thermocooling device cooling plate in order to lower the localized brain temperature as a neuroprotective measure in a post-stroke condition. Alternatively, the thermocooling device 10 is used to cool localized regions of the brain in a brain trauma patient as a way of lowering cerebral metabolic requirements and minimizing brain edema. Furthermore, the thermocooling device 10 can be used in any post-operative trauma situation when the possibility of cerebral edema exists such that the cerebral edema is desired to be abated or minimized. The above described device can be used in other parts of the body in instances where local tissue temperature needs to be controlled or modulated. In such instances, thermal therapy may involve using either chilled or heated portions of the device to achieve the desired result.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A neurosurgical device for thermally affecting interior cranial tissue of a patient, the device comprising:
   a housing, the housing defining an interior volume and being at least partially insertable into an exterior opening in the patient; and
   a thermal member having a thermal input side and a thermal output side, at least a portion of the thermal member being positioned within the interior volume, one of the thermal input side and the thermal output side being arrangable to provide a temperature different than the other of the thermal input side and the thermal output side, the thermal input side imparting a thermal change to the interior cranial tissue.

2. The device of claim 1, further comprising, a contact member being in thermal communication with the thermal input side of the thermal member and being in thermal communication with the interior cranial tissue.

3. The device of claim 2, further comprising a membrane for contact with the interior cranial tissue, the membrane being in thermal contact with the contact member.

4. The device according to claim 2, wherein the contact member is configured to directly contact internal cranial tissue to be treated.

5. The device of claim 1, further comprising a surface area expansion element, the surface area expansion element having an interior volume which is fillable with a thermally-transmissive fluid, the thermally-transmissive fluid being in thermal communication with the thermal member.

6. The device according to claim 5, wherein the surface area expansion element has a width measured at a widest part and a height measured from a top to a tissue contact area, the width being at least twice the height.

7. The device according to claim 6, further comprising a fluid circulation element, the fluid circulation element including a circulation member and a distribution member.

8. The device according to claim 7, wherein the circulation member is a pump and the distribution member is at least one injection member.

9. The device according to claim 1, wherein the thermal member is configured to directly contact internal cranial tissue to be treated.

10. The device according to claim 1, further comprising a protective barrier, the protective barrier being disposed on and being in thermal communication with the thermal member.

11. The device according to claim 1, further comprising a pressure sensor, the pressure sensor measuring a pressure of the interior cranial tissue to be treated.

12. The device according to claim 1, further comprising a temperature sensor, the temperature sensor measuring a temperature of the interior cranial tissue to be treated.

13. A device for thermally affecting tissue, comprising:
   a thermal member having a thermal input side and a thermal output side;
   a thermal cartridge, the thermal cartridge having a cartridge wall defining an interior surface for receiving the thermal member;
   an insert housing, the insert housing having an insert wall defining an inner volume configured to slidably receive the thermal cartridge and the insert housing being configured to fit within an opening in a patient;
   a contact member in thermal communication with the thermal input side of the thermal member; and
   a thermal bridge provided between and in thermal communication with the thermal member and the contact member.

14. A device for thermally affecting tissue, comprising:
- a thermal member having a thermal input side and a thermal output side;
- a thermal cartridge, the thermal cartridge having a cartridge wall defining an interior surface for receiving the thermal member;
- an insert housing, the insert housing having an insert wall defining an inner volume configured to slidably receive the thermal cartridge and the insert housing being configured to fit within an opening in a patient;
- a thermal dissipation member in thermal communication with the thermal member; and
- a thermal bridge provided between and in thermal communication with the thermal member and the thermal dissipation member.

* * * * *